(12) United States Patent
Bohne (10) Patent No.: US 12,409,026 B2
(45) Date of Patent: Sep. 9, 2025

(54) BIFURCATED STENT GRAFT AND METHOD OF PRODUCTION THEREOF

(71) Applicant: JOTEC GmbH, Hechingen (DE)

(72) Inventor: Lisa Bohne, Metzingen (DE)

(73) Assignee: JOTEC GmbH, Hechingen (DE)

( * ) Notice: Subject to any disclaimer, the term of this patent is extended or adjusted under 35 U.S.C. 154(b) by 881 days.

(21) Appl. No.: 17/463,667

(22) Filed: Sep. 1, 2021

(65) Prior Publication Data

US 2021/0393393 A1 Dec. 23, 2021

Related U.S. Application Data

(63) Continuation of application No. PCT/EP2020/055614, filed on Mar. 4, 2020.

(30) Foreign Application Priority Data

Mar. 6, 2019 (EP) .................................... 19160930

(51) Int. Cl.
*A61F 2/07* (2013.01)
*A61F 2/06* (2013.01)
*A61F 2/89* (2013.01)

(52) U.S. Cl.
CPC .................. *A61F 2/07* (2013.01); *A61F 2/89* (2013.01); *A61F 2002/061* (2013.01); *A61F 2002/065* (2013.01); *A61F 2002/075* (2013.01); *A61F 2220/005* (2013.01);
(Continued)

(58) Field of Classification Search
None
See application file for complete search history.

(56) References Cited

U.S. PATENT DOCUMENTS

| | | | |
|---|---|---|---|
| 5,123,919 A | * | 6/1992 | Sauter .................. A61F 2/06 623/2.4 |
| 6,645,242 B1 | | 11/2003 | Quinn |
| 2006/0277651 A1 | | 12/2006 | Razzaghi et al. |

(Continued)

FOREIGN PATENT DOCUMENTS

| | | |
|---|---|---|
| CN | 204092277 U | 1/2015 |
| DE | 102014110013 A1 | 1/2016 |

(Continued)

OTHER PUBLICATIONS

First Office Action (Including Translation) for corresponding Chinese Patent Application No. 202080019179.9, mailed Apr. 4, 2024.
(Continued)

*Primary Examiner* — Leslie A Lopez
(74) *Attorney, Agent, or Firm* — Jason H. Vick; Amped IP LLC (57) ABSTRACT

The present invention relates to a vascular implant for implanting into a blood vessel of a patient, the vascular implant comprising a hollow-cylindrical main body with a proximal end and a distal end, a main body lumen and a longitudinal axis, and at least one hollow-cylindrical side body that branches off from the main body and comprises a side body lumen, the side body lumen being in fluid communication with the main body lumen, wherein the hollow-cylindrical main body and the at least one hollow-cylindrical side body are formed in one piece from one single planar sheet of graft material.

16 Claims, 4 Drawing Sheets

(52) U.S. Cl.
CPC .............. *A61F 2220/0058* (2013.01); *A61F 2220/0075* (2013.01); *A61F 2230/0069* (2013.01); *A61F 2240/001* (2013.01)

(56) References Cited

U.S. PATENT DOCUMENTS

| | | | |
|---|---|---|---|
| 2006/0287704 A1* | 12/2006 | Hartley | A61F 2/07 623/1.13 |
| 2007/0106368 A1 | 5/2007 | Vonderwalde | |
| 2008/0262341 A1* | 10/2008 | Boyden | G16H 20/40 604/20 |
| 2008/0281424 A1 | 11/2008 | Parry et al. | |
| 2008/0288073 A1 | 11/2008 | Renganath et al. | |
| 2009/0171440 A1* | 7/2009 | Carlson | D03D 1/0041 623/1.42 |
| 2012/0191178 A1 | 7/2012 | Laduca | |
| 2015/0250626 A1 | 9/2015 | Fischer et al. | |
| 2016/0287376 A1* | 10/2016 | Kelly | A61F 2/954 |
| 2016/0374682 A1 | 12/2016 | Leonard et al. | |
| 2019/0046317 A1 | 2/2019 | Murad et al. | |

FOREIGN PATENT DOCUMENTS

| | | |
|---|---|---|
| EP | 0709066 A1 | 5/1996 |
| JP | 2008-541949 A | 11/2008 |
| JP | 2010-517703 A | 5/2010 |
| JP | 2010-275662 A | 12/2010 |
| JP | 2015-535453 A | 12/2015 |
| WO | WO 00/49951 A1 | 8/2000 |
| WO | WO 01/66037 A2 | 9/2001 |
| WO | WO 2006/130755 A2 | 12/2006 |
| WO | WO 2008/098252 A2 | 8/2008 |

OTHER PUBLICATIONS

Notice of Reason for Refusal (Including Translation) for corresponding Japanese Patent Application No. 2021-552795, mailed Feb. 6, 2024.
International Search Report for International Application No. PCT/EP2020/055614, mailed Apr. 22, 2020.
Written Opinion for International Application No. PCT/EP2020/055614, mailed Apr. 22, 2020.
Office Action for corresponding European Patent Application No. 20708491.4, mailed Aug. 13, 2024.

* cited by examiner

BIFURCATED STENT GRAFT AND METHOD OF PRODUCTION THEREOF

CROSS-REFERENCES TO RELATED APPLICATIONS

This application is a continuation of international patent application PCT/EP2020/055614, filed on Mar. 4, 2020, designating the U.S., which international patent application has been published in English language and claims priority from European patent application 19 160 930.4, filed on Mar. 6, 2019. The entire contents of these priority applications are incorporated herein by reference.

TECHNICAL FIELD

This invention relates to a vascular implant for implanting into a branched blood vessel of a patient to restore patency of the vessel.

BACKGROUND

The present invention relates to a vascular implant for implanting into a blood vessel of a patient, the vascular implant comprising a hollow-cylindrical main body with a proximal end and a distal end, a main body lumen and a longitudinal axis, and at least one hollow-cylindrical side body that branches off from the main body and comprises a side body lumen, the side body lumen being in fluid communication with the main body lumen.

Such so-called branched vascular implants are known in the prior art. Such vascular implants, which are also referred to as endovascular grafts, are implanted for the treatment of aneurysms, occlusions or other damage in arteries. An aneurysm is understood as being a widening or bulging of an arterial blood vessel as a result of congenital or acquired changes of the wall. The bulging may affect the vessel wall as a whole or, as in the case of a so-called false aneurysm or so-called dissection, blood can flow from the lumen of the artery in between the layers of the vessel wall and can tear them apart. Non-treatment of an aneurysm, occlusions or other damage can lead to a rupture of the artery in the advanced stage, with the consequence that the patient internally bleeds.

For the treatment of aneurysms, occlusions or other damage, the vessel concerned is therefore bridged and/or stabilized by implanting a graft, in order to avoid rupturing of the vessel.

Such a graft can be applied to the vessel alone or the graft can be supported by a metal stent or stent springs successively arranged inside or outside the graft. Such a construction is referred to as stent graft.

The graft or stent graft is introduced to the blood vessel by endoluminal techniques employing suitable delivery devices, in order to restore patency of the blood vessel across the aneurysm.

At the location of the vessel at which such a vascular implant is to be inserted, blood vessels often branch off laterally, which is why upon introduction of the vascular implant of such branching locations in the vessel there is the risk of these side vessels being cut off from blood supply by the vascular implant in the main vessel or by the implant material, which can be impermeable to blood. Therefore, in these regions vascular implants often have opening also known as "fenestrations" in the graft material, in order to direct blood flowing through the vascular implant through these openings and also generally through side branches of the vascular implant, which side branches are separately provided in these openings and are being introduced into the side vessels, also into the side vessels branching off from the vessel. In this way, it is guaranteed that the regions of the body that are supplied by the side vessel are supplied with blood also.

In many cases, the vascular implants or graft/stent grafts to be introduced at such branching regions do not only have fenestrations but also side branches branching off from the main body of the vascular implant, these branches being released in the aneurysmal sac above the branching vessel and serving, for example, as a landing zone for an additional stent graft, which is implanted into the side branch and the branching vessel in order to bridge the aneurysm. In this way it is additionally guaranteed that the side vessels are supplied with blood also.

Critical regions in the human vascular system are, for example, the region of the aorta bifurcation, and also the branching of the Arteriae iliacae communes into the Arteriae iliacae externa and the Arteriae iliacae interna. With each of the branchings, it is usually necessary to ensure the supply to the vessels branching off if the aorta or the Arteriae iliacae have to be treated in this region, for example because of an aneurysm.

Vascular implants comprising side branches that are currently known and available in the prior art are usually made by attaching the side branches between the stent springs as depicted for example in U.S. Pat. No. 6,645,242B. Alternatively, as for example disclosed in EP0709066A1 a side arm graft tube is sutured into an orifice of a main graft tube.

A disadvantage of the vascular implants bearing side branches that are known in the prior art is that these vascular implants having side branches usually have an accumulation of material in the region of the branching, such as for example a nitinol ring in the side branch, by means of which the side branch is opened after expansion, or such as for example additionally sewn-in fabric rings of implant material, which in turn necessitate larger insertion systems, and, in narrow vessels, may lead to difficult handling of these vascular implants. Ring-forming sutures perpendicularly to the blood flow may also cause turbulences in the blood flow, thus increasing the risk of formation of a stenosis. Often, the side branches are also very unstable and, as a result, difficult to handle once they have been introduced into the vessel.

SUMMARY

The object of the present invention is therefore to provide a vascular implant that can be inserted easily and stably into the main vessel and into the side vessel, and consequently into the branching, whereby an accumulation of material is advantageously avoided and an undisturbed flow of blood is achieved. A further object is to provide a safe and cost effective method of producing such a vascular implant.

This and other objects are achieved according to the present invention by a development of the vascular implant for implanting into a blood vessel of a patient as defined in in the attached claims.

This object is also achieved by a method for manufacturing the vascular implant as defined in the attached claims.

The invention is therefore said to reside in a vascular implant comprising a hollow-cylindrical main body with a proximal end and a distal end, a main body lumen and a longitudinal axis, and at least one hollow-cylindrical side body that branches off from the main body and comprises a side body lumen, the side body lumen being in fluid communication with the main body lumen, wherein the hollow-cylindrical main body and the at least one hollow-cylindrical side body are formed in one piece from one single planar sheet of graft material.

Throughout the specification the term "proximal" generally denotes the position, direction or a portion or end of a component of the vascular implant that lies closer to the heart of the patient to be treated. Correspondingly the term "distal" means that position, direction or a portion or end of a component of the vascular implant according to the invention that is/leads further/furthest away from the heart of a patient in the direction of blood flow.

In one embodiment, the single planar sheet of which the vascular implant of the present application is formed from, comprises a main portion having a width corresponding to the circumference of the main body and at least two mirrored arm portions or in other words, on pair of mirrored arm portions, extending from the main portion at either side having a width corresponding to half of the circumference of the side body.

The angle at which the longitudinal axis of the arm portions are arranged relative to the longitudinal axis of the main portion also define at least a restricted range of angles at which the side body of the implant is set up in relation to the longitudinal axis of the main body.

Accordingly, in a preferred embodiment of the vascular implant of the present invention, the at least one side body branching off from the main body is set up at an angle α in relation to the longitudinal axis of the main body.

This angle can be smaller than 10° in case the main tube and the side tube are arranged in parallel to each other. On the other hand, this angle should be smaller than 90° to avoid increased turbulences in the blood flow close to the region of the bifurcation. Preferably, the angle with which the longitudinal axis of at least one side body protrudes from the main body with respect to the longitudinal axis of the main body is between 0° and smaller than 90°, in particular between 20° and 80°, and in particular between 35° and 55°, and in particular angles in the range of 40° to 50°, and still more preferably in the range between 44° and 46°, and most preferably an angle of 45°.

In the present case, this consequently also expressly includes all figures that lie between these ranges; it will be clear to a person skilled in the art that the ranges mentioned herein above also include tolerance bands that lie outside, i.e. above or below, the ranges specified, and lie within customary production and measuring tolerances.

In different embodiment of the present invention, the vascular implant according to the invention may comprise one or more side bodies, each protruding at a different angle in relation to the longitudinal axis of the vascular implant and thus, accordingly, the single planar sheet may comprise several pairs of mirrored arm portions.

The vascular implant or its hollow-cylindrical main body may have a uniform diameter, or else different diameters, over its overall length. This diameter is determined by the width of the main portion of the single planar sheet. The same applies *mutis* mutandis to the side body and the pairs of mirrored arm portions if the single planar sheet.

In a further preferred embodiment, the main portion of the single planar sheet of which the vascular implant of the present application is formed from, is divided partially to form a proximal common main portion and two main portion legs toward the distal end. This embodiment allows for more precise shaping of the main body.

In a further embodiment of the present invention, the single planar sheet of which the vascular implant of the present application is formed from, comprises a main portion as depicted above, which may or may not include main portion legs and at least two mirrored arm portions extending from the main portion at either side wherein at least two mirrored arm portions (one pair of mirrored arm portions) further comprise secondary side arm portions extending from the arm portions.

Employment of such a sheath leads to an alternative embodiment of a vascular implant according to the present application having one or more secondary side bodies branching off from a side body.

The angle at which the longitudinal axis of the secondary side arm portions are arranged relative to the longitudinal axis of the arm portion also define at least a restricted range of angles at which the longitudinal axis of the secondary side body of the implant is set up in relation to the longitudinal axis of the side body. This angle can be smaller than 10° in case the side tube and the secondary side tube are arranged in parallel to each other. Preferably, the angle with which the longitudinal axis of the at least one secondary side body protrudes from side body with respect to the longitudinal axis of the side body is between 0° and 90°, in particular from 20° and 80°, and in particular between 35° and 55°, and in particular angles in the range of 40° to 50°, and still more preferably in the range between 44° and 46°, and most preferably 45°.

As the vascular implant of the present invention is formed from a single layer sheet, the edges of the planar sheet are bonded to each other to form a hollow cylindrical structure of the implant, namely to form the hollow-cylindrical main body and the least one hollow-cylindrical side body and optionally the hollow-cylindrical secondary side body. Bonding techniques suitable for closing the seams of the implant include welding, gluing, stitching or sewing/suturing, where sewing, in particularly hand sewing is preferred. In a preferred embodiment the bond is impermeable to blood or liquid tightly sealed.

Suture materials currently used in the fields of surgery and stent implant technology can be used as suture material for sewing the graft material, and such suture materials generally consist of polyester, polyurethane, polytetrafluoroethylene, polyethylene, ultrahigh molecular weight polyethylene (UHMWPE), polypropylene.

In a further preferred embodiment of the present application the vascular implant of the present invention further comprises a dart at the site where the side body branches off, the dart extending from the distal end of the side body opening in the main body along a portion of the proximal end of the side body. Such a dart allows for an improved form of the branched vascular implant. It allows for a smooth inside surface of the implant and a good hollow-cylindrical shape of the main body and the side body. Also, by adjusting the width and length of the dart, the angle at which the longitudinal axis of the side body protrudes from the longitudinal axis of the main body may be adjusted, too.

In case the vascular implant further comprises a secondary side body, the implant may also comprise a dart at the site where the secondary side body branches off, with the dart extending from the distal end of the secondary side body opening in the side body along a portion of the proximal end of the secondary side body.

In one embodiment the dart can be formed by folding a part of the graft material in the distal part of the branching-off region in the main tube with the dart pointing to each side of the side tube in a proximal direction. In a further preferred embodiment, the folds are secured by sewing.

In a further embodiment the dart can be formed by incisions into the sheet of graft material at the distal end of the dissection of the side arm in the main portion substantially parallel to the longitudinal axis of the main body. These incisions are then bonded together, when forming the tubular members out of the sheet of graft material. In a further preferred embodiment, the incisions are bonded by sewing.

The graft material, namely the planar sheet of graft material may be woven, braided, knitted, electro-spun, or sputtered. There are numerous textile fabrics, textile composite materials and medical textiles suitable as graft material in vascular implants known to the skilled person. In preferred embodiments, the planar sheet of graft material of any of the above-mentioned vascular implants is made from one or more polymers or copolymers thereof selected from Polyurethane, Polyether, Polyester, Polyamide, Polyethyleneterephthalate, Polytetrafluorethylen, or expanded Polytetrafluorethylen.

In a further alternative embodiment, the vascular implant of the present invention has at least one further additional side body branching off from either the main body or from any of the side bodies, wherein the additional side body is made from a second piece of graft material and wherein the proximal end of the additional side body is attached to the circumference of an aperture in the graft material of the main body or any of the side bodies.

In preferred embodiment, the vascular implant of the present invention further comprises one or more stent rings successively arranged over the longitudinal axis of at least a portion of the main body and optionally of at least a portion of any of the side bodies, the stent rings being transformable from a compressed state into a self-expanded state.

In the present case, a "stent ring" denotes any device or a structure that provides a force of expansion and/or a supporting function for a prosthesis.

In a further preferred embodiment, in the vascular implant of the present invention the stent rings are one-piece stent springs successively arranged over the longitudinal axis of the main body and circumferentially meandering respectively, perpendicularly in relation to the longitudinal axis. The stent springs are connected to the graft material, thus, the stent springs are connected to one another via the graft material only and not between one another.

Further, the circumferentially meandering stent springs have pointed arches that alternately face toward the proximal end and the distal end of the main body and parallel to the longitudinal axis thereof. In the self-expanded state the at least one side body branching off from the main body is set up at an angle in relation to the longitudinal axis of the main body, the angle being stabilized by at least one pointed arch of a stent spring of the main body angularly protruding in a preformed way in relation to the longitudinal axis of the main body in the self-expanded state.

In a further preferred embodiment of the present invention, dart of the graft material extends from the distal end of the side body opening in the main body up to a position adjacent to a leg of the pointed arch of the stent spring angularly protruding in relation to the longitudinal axis of the main body. The dart does not cross any of the stent springs.

The stent rings or stent springs may be attached to the graft material of the vascular implant of the present invention by gluing, welding, or sewing. When sewing, the same suture materials as depicted above can be used as suture material for sewing the stent rings the graft material.

Presently, a "stent spring" is understood as being any one-piece, annular element which is compressible due to its material, and which, after removal of the compressing pressure, can expand again in the manner of a spring.

"Meandering" is understood in the present case as meaning any serpentine or looped shape of the stent spring or the stent wire, each stent spring being formed as one part, i.e. from one stent spring ring circumferentially meandering manner.

In this context, a "one-piece stent spring circumferentially meandering", presently, is an annular stent element that expands and can be compressed in a spring-like manner and is circumferential and meandering, wherein the wave crest and wave trough, which form a phase, alternate.

A "pointed arch" is respectively formed by two legs and a vertex or lowest point herein between.

"At least one pointed arch" presently means that the side body is extended by the protrusion or setting out of a single pointed arch of a stent spring, or else by two or more pointed arches. In a preferred embodiment, two pointed arches of a stent spring are set out. In principle, the plurality of the pointed arches circumferentially meandering form the stent spring of the main body, and the protruding pointed arch/pointed arches form(s) the branching point for the side body.

By definition, the stent springs are not directly connected to one another, and do not have any connecting legs or struts or similar connecting elements there between. The stent springs are only connected to one another by way of the implant material or graft material to which the stent springs are attached, whereby an "indirect connection" is created between the stent springs.

Presently, the expression "stent graft" is intended to encompass a prosthesis that has one or more stents (or stent springs) and also an implant ("graft") material connected thereto, which forms a lumen through at least one portion of the prosthesis.

According to a further embodiment of the vascular implant according to the invention, the angle at which the at least one side body is set out/protrudes from the main body is in this case specifically made to match the vessel to be treated or the vessel portion to be treated. This can be defined exactly in advance by the doctor performing the treatment. It goes without saying that, according to a further embodiment of the vascular implant according to the invention, the respective precise angle may vary from vascular implant to vascular implant. In general, due to the stent spring with the at least one pointed arch protruding at an angle, the position of the side branch is more flexible in vivo than if it is implemented without an angle. There is less risk of the side branch kinking.

In one further embodiment of the vascular implant according to the invention, the at least one side body has a portion with at least one side-body stent spring arranged perpendicularly in relation to its side-body longitudinal axis and circumferentially meandering, the side-body stent spring being fixed to the side body graft, wherein the at least one side-body stent spring and the stent spring of the main body angularly protruding are only being connected via the graft material and not with one another.

This embodiment has the advantage that the at least one side body of the vascular implant according to the invention also has a stented portion, which ensures secure anchorage for a second stent graft, which leads into the branching vessel to bridge the aneurysmal sac.

In the present case, a "stented portion" is understood as to encompass any portion of a vascular implant that has at least one stent or a stent spring element connected with a prosthetic material.

By contrast thereto, in the present case an "unstented" portion is understood as meaning any portion of a vascular implant that is only formed from prosthetic material.

According to a development of the vascular implant according to the invention, the stent springs are connected to the implant material indirectly connecting them, preferably being sewn to the implant material. The same also applies to the stent springs of the side body. In this case, the stent springs may either be sewn in the internal lumen of the vascular implant, i.e. internally to the implant material, or else externally onto the implant material.

According to a preferred embodiment of the vascular implant according to the invention, it has between one and four, i.e. one, two, three or four, side branches set up/protruding at an angle from the main body.

Consequently, the vascular implants according to the invention can also be advantageously introduced into vessel portions at which a number of side blood vessels branch off. Depending on the respective patient or vascular situation, one skilled in the art will be able to determine how many side branches are required for the vascular implant to be used.

It goes without saying that several protruding pointed arches may be provided on different stent springs, depending on the position of the branching side blood vessels.

The invention is further said to reside in a method for manufacturing the vascular implant according to the present invention, the method comprising the steps of
  (i) providing a planar sheet of graft material, and
  (ii) bonding the edges of the planar sheet to each other by welding, gluing, stitching or sewing to form the hollow-cylindrical main body and the least one hollow-cylindrical side body.

In a further preferred embodiment, where the vascular implant is a stent graft, the method for manufacturing the vascular implant according to the present invention further comprises the steps of:
  (iii) providing one or more stent springs,
  (iv) setting up the stent springs in relation to the longitudinal axis of the vascular implant, and
  (v) fixing, preferably sewing the at least one stent rings to the hollow-cylindrical main body.

In an even more preferred embodiment, the method for manufacturing the vascular implant according to the present invention comprises the steps of:
  (vi) providing a stent spring having pointed arches that alternatively face toward the top and bottom of the stent spring and parallel to the longitudinal axis thereof and at least one pointed arch, preferably two neighbored pointed arches which are angularly protruding in relation to the longitudinal axis of the stent spring,
  (vii) setting up the stent spring providing a pointed arch protruding at an angle in relation to the longitudinal axis of the vascular implant and aligning the pointed arch protruding at an angle to the side branch likewise protruding at an angle,
  (viii) fixing, preferably sewing the at least one stent rings to the hollow-cylindrical main body.

Further advantages and features can be derived from the following description and the accompanying drawing.

It goes without saying that the features mentioned above and still to be explained below can be used not only in the combination respectively specified, but also in other combinations or on their own without departing from the scope of the present invention.

BRIEF DESCRIPTION OF THE DRAWINGS

Exemplary embodiments of the invention are represented in the drawings and are described in more detail below with reference thereto.

DESCRIPTION OF PREFERRED EMBODIMENTS

Figure 1:
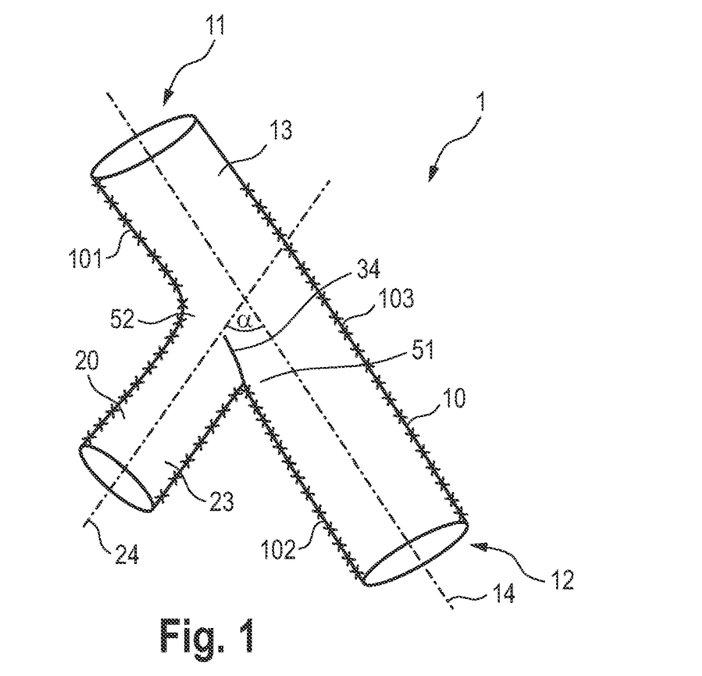
FIG. 1 shows an exemplary embodiment of a vascular implant of the present invention having a side body in a schematic lateral plan view.

FIG. 1 depicts an exemplary embodiment of a vascular implant of the present invention having a side body in a schematic lateral plan view. The vascular implant 1 comprises a hollow-cylindrical main body 10 with a proximal end 11 and a distal end 12, a main body lumen 13 and a longitudinal axis 14, and at least one hollow-cylindrical side body 20 that branches off from the main body 10 and comprises a side body lumen 23, the side body lumen 23 being in fluid communication with the main body lumen 13.

The angle $\alpha$ at which the longitudinal axis 24 of the at least one side body 20 is arranged relative to the longitudinal axis 14 of the main body is about 45° in the branched graft of FIG. 1. Though, it has to be noted that this is only for illustration and the angle may be between 0° and 90°, preferably between 20° and 90°, preferably between 35° and 55°, preferably between 40° to 50°, and still more preferably in the range between 44° and 46°, and preferably 45°.

The hollow-cylindrical main body 10 and the at least one hollow-cylindrical side body 20 are formed in one piece from one single planar sheet of graft material 30. The vascular implant as shown in FIG. 1 is formed from a single planar sheet of graft material 30 as shown in FIG. 3B or FIG. 3C. The planar sheet 30 illustrated in FIGS. 3B and 3C comprises a main portion 31' having a width corresponding to the circumference of the main body 10 and two mirrored arm portions 32, 32' extending from the main portion at either side having a width corresponding to half of the circumference of the side body 20. Further, as can be seen in FIGS. 3B and 3C, the portion forming the main tube is divided partially to form a common main portion 31' on the proximal side and two main portion legs 311, 311' on the distal side. In the implant 1 of FIG. 1, the respective edges of the planar sheet 30 are bonded or sealed to each other by sewing the edges A and A' together, B and B' together, and C and C' together. The vascular implant of FIG. 1 thus shows three longitudinal seams 101(A-A'), 102(B-B'), 103(C-C'). Seam 101 extends longitudinally from the proximal end of the main body 10 to the distal end of the side tube 20. Seam 102 extends longitudinally from the opposite side of the distal end of the side body to the distal end of the main body 10. Seam 103 extends longitudinally the opposite side of the distal end of the main body 10 to a site distal from the proximal end of the main tube 10 and proximal of the side tube 20.

Figure 3A:
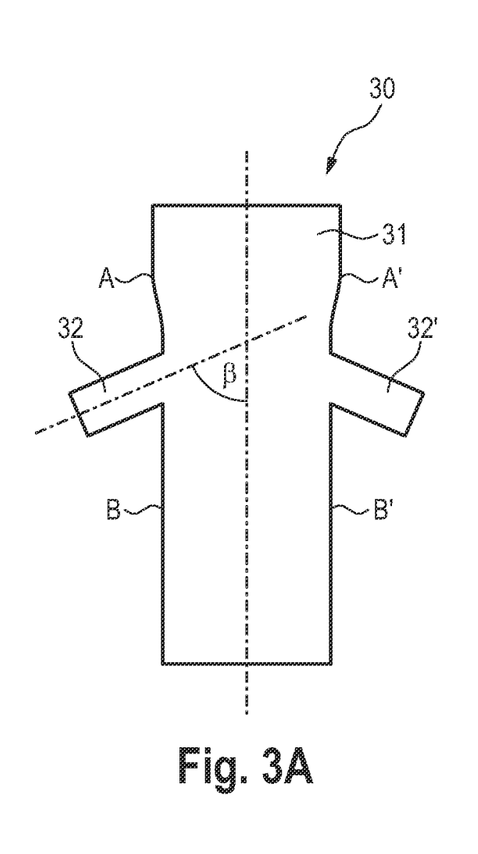
FIGS. 3A, 3B and 3C show schematic views of different embodiments of the single planar sheet of graft material for a vascular implant of the present invention.
Figure 3B:
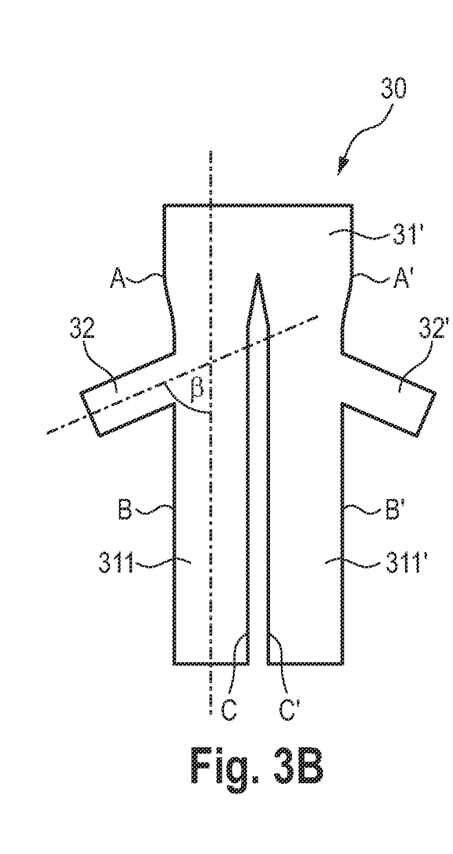
Figure 3C:
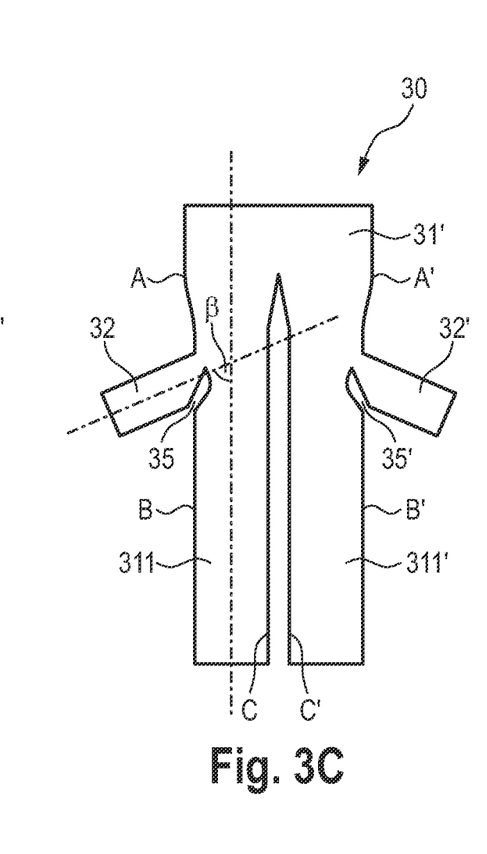

It will be obvious to the skilled person, that a graft as depicted in FIG. 1 may also be formed of a planar sheet of graft material as shown in FIG. 3A.

FIG. 3A is a schematic view of a planar sheet 30 comprising a main portion 31 having a width corresponding to the circumference of the main body 10 and two mirrored arm portions 32, 32' extending from the main portion at either side having a width corresponding to half of the circumference of the side body 20.

When connecting edges A and A' as well as B and B', a vascular implant according to FIG. 1 is formed, except that in this case seam 103 is missing, as the graft material of FIG. 3A is not sliced laterally.

The angle β at which the side portions or the longitudinal axis of the arm portions are arranged relative to the longitudinal axis of the main portion is also about 45° in planar sheet of FIGS. 3A to 3C.

It has to be understood that this angle may be between 0° and 90°, preferably between 20° and 90°, preferably between 3° and 55°, preferably between 40° to 50°, and still more preferably in the range between 44° and 46°, and preferably 45°.

Generally, the angle β in the planar sheet determines also a certain range for angle α in the vascular implant formed from the planar sheath.

As also illustrate in FIG. 1, the vascular implant further comprises a dart 34 extending from the distal end of the side body opening in the main body 51 along a portion of the "virtual" proximal end of the side body 52.

Generally, the depth and length of this dart also allows adjustment of the angle α in the vascular implant.

The dart 34 can be formed by folding a part of the graft material in the distal part of the branching-off region in the main tube with the dart pointing to each side of the side tube in a proximal direction. Preferably, the folds are secured by sewing. This embodiment applies when using a planar sheet according to e.g. FIG. 3A or 3B.

Alternatively, the dart 34 can be formed by incisions 35 and 35' into the sheet of graft material 30 at the distal end of the dissection of the side arm in the main portion substantially parallel to the longitudinal axis of the main body as depicted in FIG. 3C. These incisions 35, 35' are then bonded together, when forming the tubular members out of the sheet of graft material. Preferably, the incisions are bonded by sewing.

It has to be noted, that the hollow-cylindrical main body 10 of the vascular implant with the main body lumen 13, has a diameter which may or may not change over the length. Also, the hollow-cylindrical side body 20 of the vascular implant with the main body lumen 23, has a diameter which may or may not change over the length.

Figure 2:
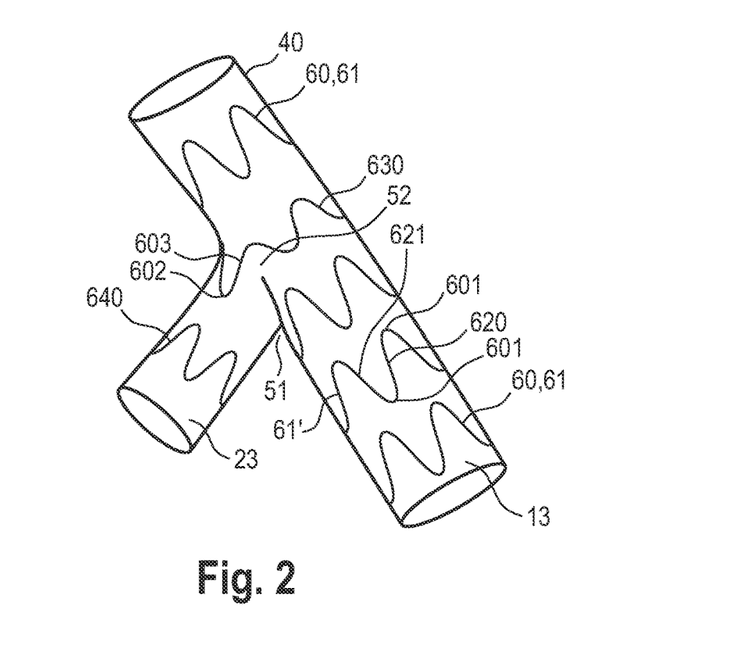
FIG. 2 shows another exemplary embodiment of a vascular implant of the present invention having a side body and stent rings in a schematic lateral plan view.

FIG. 2 shows a schematic lateral plan view of an exemplary embodiment of a vascular implant 1 according to the invention, with, by way of example, five stent rings 60 are successively arranged over the longitudinal axis of the vascular implant 1.

As exemplified in FIG. 2 the stent rings 60 are one-piece stent springs 61 successively arranged over the longitudinal axis 14 of the main body 10 and circumferentially meandering respectively, perpendicularly in relation to the longitudinal axis 14.

As shown in FIG. 2 with reference to stent spring 61', a pointed arch 601 is formed by two legs 620, 621 and a vertex 601'.

The stent springs are connected to one another indirectly by the graft material, i.e. not directly by way of struts or the like. The vascular implant shown in FIG. 2 therefore has a portion that is "stented", or it consists of such a portion in case all of the graft material 40 is supported by stent springs that are attached to the implant material at specific distances from one another. It goes without saying that the vascular implant may also have further portions that consist either of an implant material supported by a stent wire mesh or a laser-cut stent, or of an unstented implant material, or of a stent wire mesh without implant material.

Returning to FIG. 2, FIG. 2 also reveals that the stent spring has two setup pointed arches 602 (of which the second arch is not shown), which because of the way in which they are shaped laterally protrude at an angle with respect to the longitudinal axis of the vascular implant. The other pointed arches 601 of all the stent springs 61 run parallel to the longitudinal axis of the vascular implant. This protruding or setting up of the pointed arches 602 of the stent spring 630 has the effect of defining a side body or side branch 23a; this side branch 23a offers an anchoring zone in the side vessel for a stent graft/stent-graft portion, for example a covered stent graft/stent-graft portion, which is inserted into a side vessel branching off from a main blood vessel.

In the example shown in FIG. 2, the side body 20 also has a side-body stent spring 640 of its own, which consequently does not form a stent spring of the main body 10 of the vascular implant 1. The side-body stent spring 640 is indirectly connected by the graft material to the set-out pointed arch 602 of the stent spring 630 of the main body 10.

In the example shown in FIG. 2, the stent springs 61, 630 and the side-body stent spring 640 are sewn onto the graft material 40 consisting of the sheet 30.

The stent rings or springs may be made of any material suitable to allow the stent ring or spring to provide a force of expansion and/or a supporting function. Preferred materials are metal alloys, such as stainless steels, nickel-titanium alloys, tantalum, cobalt-chromium alloys, and magnesium alloys. A preferred material for the stent rings or springs is Nitinol (nickel-titanium alloys) which imparts self-expanding properties to the stent rings or springs.

Referring back to FIG. 2, the dart 34 or seam located at the distal side of the branch-off of the side body 20 from the main body 10 of the vascular implant 1 extends from the distal end of the side body opening in the main body 51 up to a position adjacent to a leg 603 of the pointed arch 602 of the stent spring 630 angularly protruding in relation to the longitudinal axis of the main body, but not being in contact with the stent spring. This is to provide good support of the vascular implant in the region of the branch-off, but also excellent form and smoothness of the inner lumen, avoiding multiple material overlaps or even folds.

Figure 4:
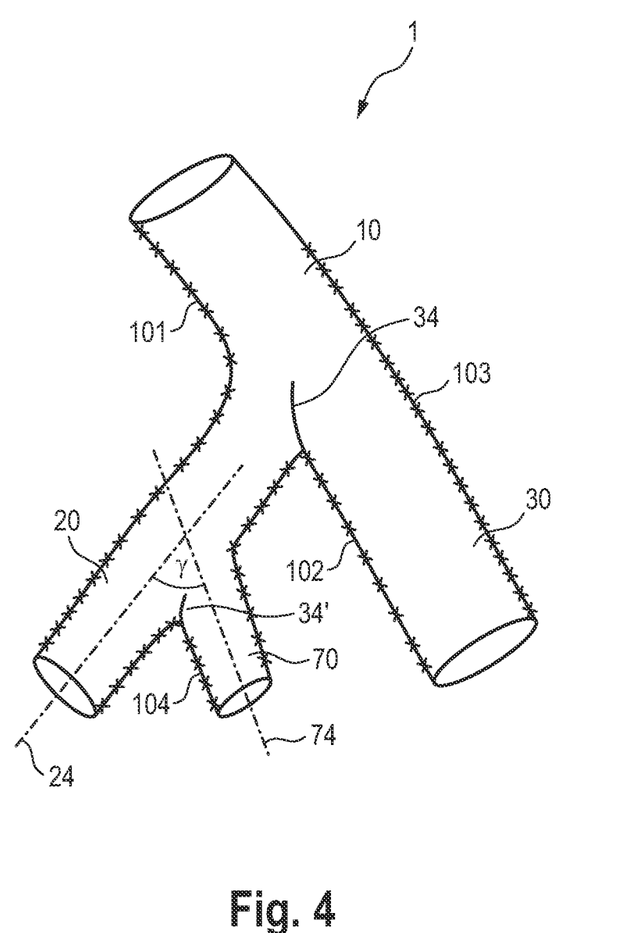
FIG. 4 shows a further exemplary embodiment of a vascular implant of the present invention having a bifurcated side body in a schematic lateral plan view.

In FIG. 4, a vascular implant 1 of the present invention is shown, which has a branched side body. This vascular implant is generally built up according as is the vascular implant 1 depicted in FIG. 1, which is referred to therewith, but having an additional branch or secondary side body which has one or more secondary side bodies 70 branching off from a side body 20.

The angle γ at which the secondary side body 70 or the longitudinal axis of the second side body 74, respectively, is arranged relative to the longitudinal axis 24 of the side body is about 45° in the branched graft of FIG. 4. Though, it has to be noted that this is only for illustration and the angle may be between 0° and 90°, preferably between 20° and 90°, preferably between 35° and 55°, preferably between 40° to 50°, and still more preferably in the range between 44° and 46°, and preferably 45°.

Figure 5:
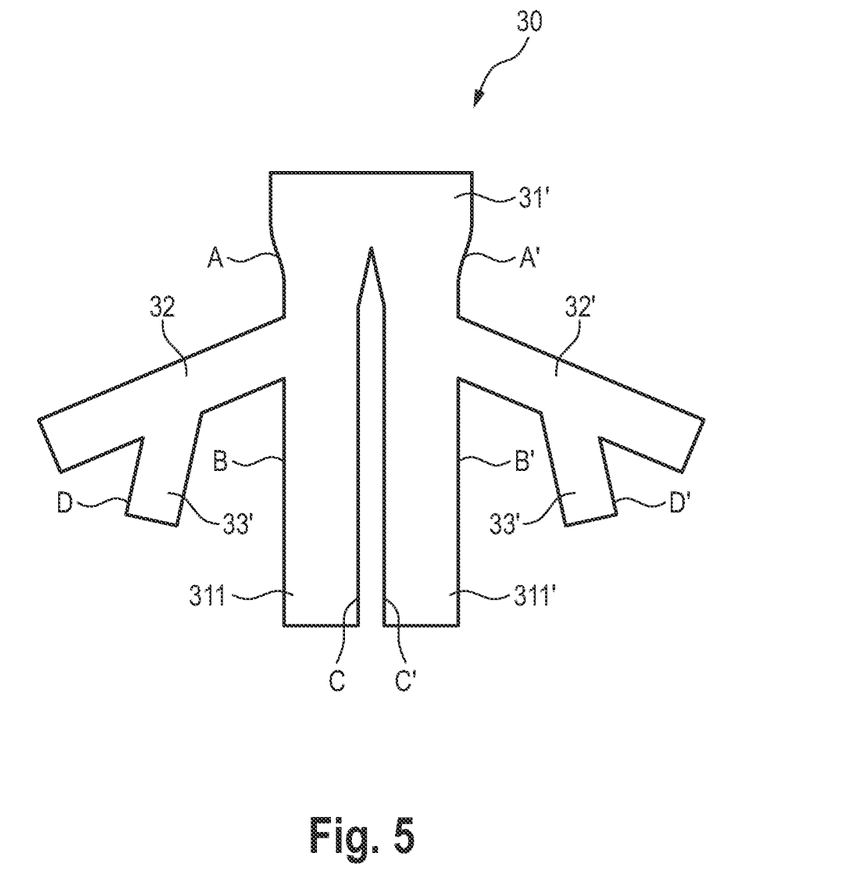
FIG. 5 shows a schematic view of an exemplary single planar sheet of graft material employed for the exemplary vascular implant depicted in FIG. 4

The hollow-cylindrical main body 10, the hollow-cylindrical side body 20, and the hollow-cylindrical secondary side body 70 are formed in one piece from one single planar sheet of graft material 30. The vascular implant as shown in FIG. 4 is formed from a single planar sheet of graft material 30 as shown exemplarily in FIG. 5. The planar sheet 30 illustrated in FIG. 5 comprises a main portion 31' having a width corresponding to the circumference of the main body 10 and two mirrored arm portions 33, 33' extending from the secondary portions 32, 32' at a predetermined angle and having a width corresponding to half of the circumference of the secondary side body 70. Further, the main portion 31 is divided partially to form a common main portion 31' on the proximal side and two main portion legs 311, 311' on the distal side.

In the implant 1 of FIG. 4, the respective edges of the planar sheet 30 are bonded or sealed to each other by sewing the edges A and A' together, B and B' together, C and C', and D and D' together. The vascular implant of FIG. 4 thus shows four longitudinal seams 101(A-A'), 102(B-B'), 103 (C-C'), and 104(D-D'). Seam 101 extends longitudinally from the proximal end of the main body 10 to the distal end of the side tube 20. Seam 102 extends longitudinally from the opposite side of the distal end of the second side body to the distal end of the main body 10. Seam 103 extends longitudinally the opposite side of the distal end of the main body 10 to a site distal from the proximal end of the main tube 10 and proximal of the side tube 20. Seam 104 extends longitudinally from the distal end of the side body to the distal end of the secondary side body.

Further, as depicted in FIG. 4, the vascular implant has a dart 34, 34' at each dissection of the graft, the first dart 34 extending from the distal end of the side body opening in the main body 51 along a portion of the "virtual" proximal end of the side body 52 and a second dart 34' extending from the distal end of the second side body opening in the side body 51 along a portion of the "virtual" proximal end of the second side body.

The vascular implant according to any of the prescribed embodiments of the present invention is easy to produce as the graft is made from a single piece of graft material and the bonds or suture is/are straight. This allows more effective material preparation and also more effective and secure bonding. Also, the resulting graft is safer to produce, as the branch cannot be pulled out of the main body. Another advantage is its smoothness in the region of the branch connection as no bonds or material accumulation exists in the graft vertical to the blood blow.

What is claimed is:

1. A vascular implant configured for implantation into a blood vessel of a patient, the vascular implant comprising:
a hollow-cylindrical main body with a proximal end and a distal end, a main body lumen and a longitudinal axis, and at least one hollow-cylindrical side body that branches off from the main body and comprises a side body opening in the main body and a side body lumen, the side body lumen being in fluid communication with the main body lumen, wherein the hollow-cylindrical main body and the at least one hollow-cylindrical side body are formed in one piece from one single planar sheet of graft material, wherein the vascular implant further comprises a dart extending from a distal end of the side body opening in the main body towards and along a portion of the proximal end of the side body opening.

2. The vascular implant according to claim 1, wherein the single planar sheet comprises a main portion having a width corresponding to the circumference of the main body and at least two mirrored arm portions extending from the main portion at either side having a width corresponding to half of the circumference of the side body.

3. The vascular implant according to claim 2, wherein the main portion is divided partially to form a common main portion and two main portion legs.

4. The vascular implant according to claim 2, wherein the at least two mirrored arm portions further comprise secondary side arm portions extending from the arm portions.

5. The vascular implant according to claim 1, wherein the single planar sheet of graft material has edges A,A',B,B',C, C', wherein the edges A,A',B,B',C,C' are bonded to each other by welding, gluing, stitching or sewing to form the hollow-cylindrical main body and the least one hollow-cylindrical side body.

6. The vascular implant according to claim 1, wherein the planar sheet of graft material is woven, braided, knitted, electro-spun, or sputtered.

7. The vascular implant according to claim 1, wherein the planar sheet of graft material is made from one or more polymers or copolymers thereof selected from Polyurethane, Polyether, Polyester, Polyamide, Polyethyleneterephthalate, Polytetrafluorethylen, or expanded Polytetrafluorethylene.

8. The vascular implant according to claim 1, wherein the vascular implant has one or more secondary side bodies branching off from a side body.

9. The vascular implant according to claim 1, wherein the vascular implant has at least one further additional side body branching off from either the main body or from any of the side bodies, wherein the additional side body is made from a second piece of graft material and wherein the proximal end of the additional side body is attached to the circumference of an aperture in the graft material of the main body or any of the side bodies.

10. The vascular implant according to claim 1, wherein a longitudinal axis of at least one side body branching off from the main body is set up at an angle α in relation to the longitudinal axis of the main body.

11. The vascular implant according to claim 1, further comprising one or more stent rings successively arranged over the longitudinal axis of at least a portion of the main body and optionally of at least a portion of any of the side bodies, the stent rings being transformable from a compressed state into a self-expanded state.

12. The vascular implant according to claim 11, wherein the one or more stent rings comprise a plurality of stent rings, wherein the stent rings are one-piece stent springs successively arranged over the longitudinal axis of the main body and circumferentially meandering respectively, perpendicularly in relation to the longitudinal axis, the stent springs being connected to the graft material of the main body and/or any of the side bodies, the stent springs being connected to one another via the graft material only and not between one another, and
wherein the circumferentially meandering stent springs have pointed arches that alternately face toward the proximal end and the distal end of the main body and parallel to the longitudinal axis thereof,
wherein, in the self-expanded state, a longitudinal axis of the at least one side body branching off from the main body is set up at an angle α in relation to the longitudinal axis of the main body, the angle being stabilized by at least one pointed arch of a stent spring of the main body angularly protruding in a preformed way in relation to the longitudinal axis of the main body in the self-expanded state.

13. The vascular implant according to claim 12, wherein the dart extends from the distal end of the side body opening in the main body up to a position adjacent to a leg of the pointed arch of the stent spring angularly protruding in relation to the longitudinal axis of the main body.

14. A method for manufacturing the vascular implant of claim 1, wherein the vascular implant comprises a hollow-cylindrical main body with a proximal end and a distal end, a main body lumen and a longitudinal axis, and at least one hollow-cylindrical side body that branches off from the main body and comprises a side body lumen, the side body lumen being in fluid communication with the main body lumen, wherein the hollow-cylindrical main body and the at least one hollow-cylindrical side body are formed in one piece from one single planar sheet of graft material, wherein the vascular implant further comprises a dart extending from the distal end of the side body opening in the main body along a portion of the proximal end of the side body, the method comprising:
  (i) providing a planar sheet of graft material, the planar sheet of graft material having edges A, A', B, B', C, C', and
  (ii) bonding the edges A, A', B, B', C, C' of the planar sheet to each other by welding, gluing, stitching or sewing to form the hollow-cylindrical main body and the least one hollow-cylindrical side body
  wherein the dart is formed by folding a part of the graft material in a distal part of a branching-off region in the main body with the dart pointing to each of a first side and a second side of the side body in a proximal direction, the folds being secured by sewing, or
  wherein the dart is formed by incisions into the sheet of graft material at a distal end of a dissection of the side body in the main body substantially parallel to the longitudinal axis of the main body, the incisions being bonded together, when forming the side body out of the sheet of graft material.

15. The vascular implant of claim 1, wherein the dart is formed by folding a part of the graft material in a distal part of a region, where the at least one hollow-cylindrical side body branches off from the main body, in the main body, with the dart pointing to each of a first side and a second side of the side body in a proximal direction.

16. The vascular implant of claim 1, wherein the dart is formed by formed by incisions into the sheet of graft material at a distal end of a dissection of the side body in the main body substantially parallel to the longitudinal axis of the main body, the incisions being bonded together when forming the side body out of the sheet of graft material.

* * * * *